United States Patent [19]
Burnham et al.

[11] Patent Number: 5,947,053
[45] Date of Patent: Sep. 7, 1999

[54] WEAR-THROUGH DETECTOR FOR MULTILAYERED PARTS AND METHODS OF USING SAME

[75] Inventors: Jay Burnham, East Fairfield; Harold G. Linde, Richmond; Nicholas N. Mone, Jr.; Ronald A. Warren, both of Essex Junction, all of Vt.

[73] Assignee: International Business Machines Corporation, Armonk, N.Y.

[21] Appl. No.: 09/005,634

[22] Filed: Jan. 9, 1998

[51] Int. Cl.⁶ .......................... G01B 15/00; G01B 21/08; G21K 5/04; G21K 5/08

[52] U.S. Cl. .......................... 116/208; 73/86; 250/396 R; 250/492.2; 250/492.21

[58] Field of Search ........................ 116/208; 73/86; 250/396 R, 423 R, 492.2

[56] References Cited

U.S. PATENT DOCUMENTS

| | | |
|---|---|---|
| 4,982,767 | 1/1991 | Pezzoli et al. .......................... 139/449 |
| 5,126,575 | 6/1992 | White . |
| 5,134,301 | 7/1992 | Kamata et al. . |
| 5,146,098 | 9/1992 | Stack . |
| 5,187,542 | 2/1993 | Madzsar .................................. 356/300 |
| 5,262,652 | 11/1993 | Bright et al. . |
| 5,335,373 | 8/1994 | Dangman et al. ........................ 2/161.7 |
| 5,357,636 | 10/1994 | Dresdner, Jr. et al. .................. 2/161.7 |
| 5,396,076 | 3/1995 | Kimura . |
| 5,517,077 | 5/1996 | Bright et al. . |
| 5,554,852 | 9/1996 | Bright et al. . |
| 5,559,337 | 9/1996 | Ito et al. . |
| 5,625,185 | 4/1997 | Laser . |
| 5,629,528 | 5/1997 | Jost et al. .......................... 250/492.21 |
| 5,640,020 | 6/1997 | Murakoshi et al. ............... 250/492.21 |

*Primary Examiner*—Benjamin Utech
*Assistant Examiner*—Donald L. Champagne
*Attorney, Agent, or Firm*—Whitham, Curtis & Whitham; James M. Leas

[57] ABSTRACT

The present invention relates to wear-through detection in multilayered parts. This invention specifically encompasses, in one aspect, wear-through detection in semiconductor vacuum processing systems in which a wear indicator that will release a detectable constituent upon exposure to processing conditions is used inside the semiconductor vacuum processing tool. This invention permits real time detection of wear during operation of semiconductor vacuum processing equipment.

18 Claims, 9 Drawing Sheets

1 - ION SOURCE
12 - EXTRACTION ELECTRODE
13 - GROUND ELECTRODE
14 - SOURCE EXIT APERATURE
15 - LINER
16 - STRIKER PLATE
 - ANALYZER EXIT APERATURE
8 - MIRROR

WEAR-THROUGH DETECTOR FOR MULTILAYERED PARTS AND METHODS OF USING SAME

BACKGROUND OF THE INVENTION

1. Field of the Invention

The invention relates to wear-through detection in multilayered parts, and, more particularly, to wear-through detection in semiconductor vacuum processing systems.

2. Description of the Related Art

Figures 1A, 1B, 1C:
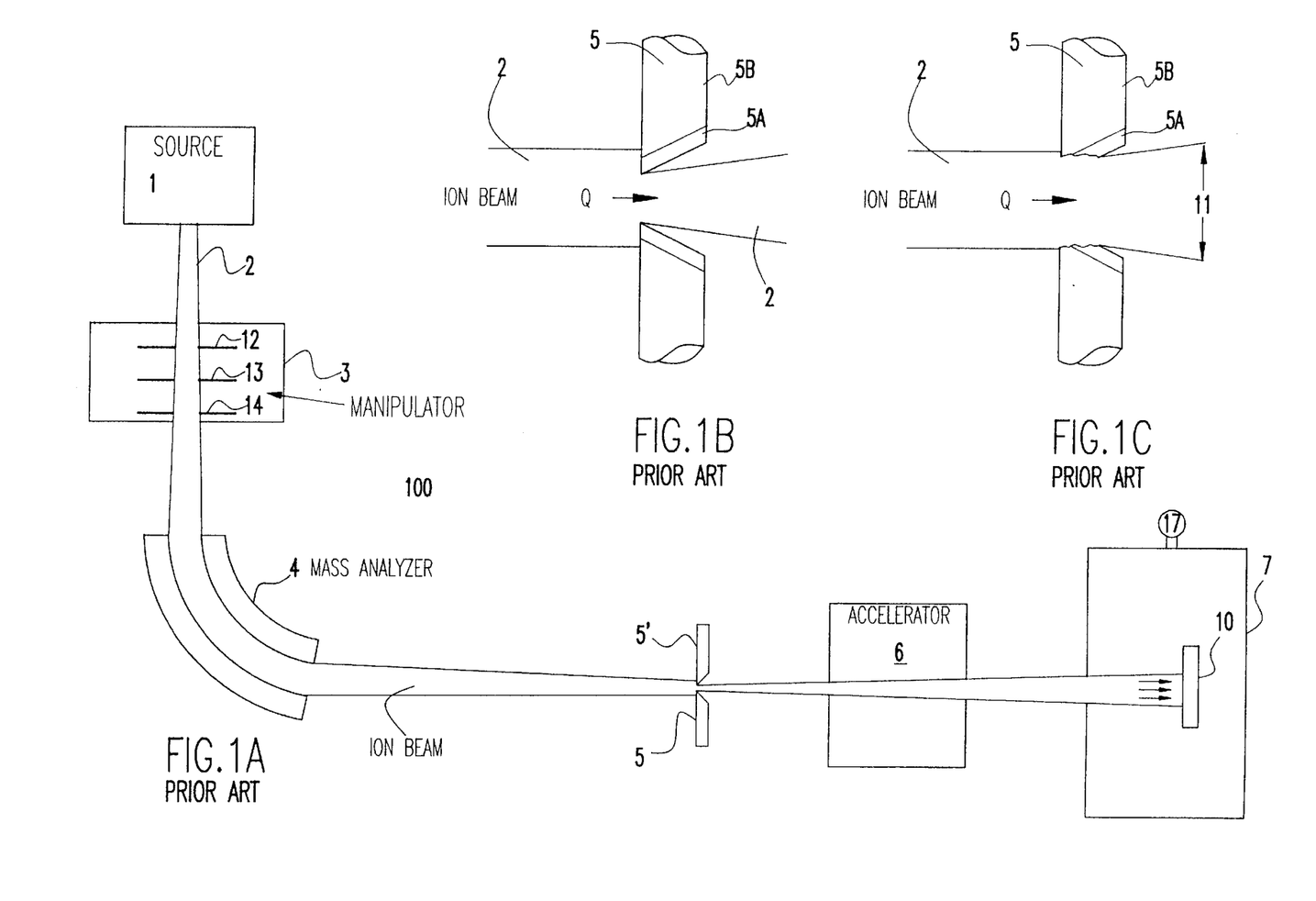
FIG. 1A is a simplified overall schematic diagram of a known ion implantation device equipped with an aperture member.
FIG. 1B is an enlarged view of an unused mass resolving aperture of the ion implant system shown in FIG. 1A.
FIG. 1C is another enlarged view of a mass resolving aperture of the ion implant system shown in FIG. 1A after incurring ion beam wear.

The use of ion implantation equipment to introduce conductivity-altering dopants into semiconductor wafers has become an integral part of the fabrication of semiconductor devices. A simplified schematic of a representative known ion implanter system 100 is shown in FIG. 1A. An ion source 1 generates positively charged dopant particles by known means which are directed as an ion beam 2 along a beam path toward a target 10, typically a semiconductor wafer, housed within target chamber 7. A manipulator 3 having extraction electrode 12, ground electrode 13, and source exit aperture 14, extracts and initiates the travel of the ion beam 2 along the beam path. Along the beam path, the ion beam 2 is deflected and focused by mass analyzer 4. The mass analyzer 4 uses magnetic forces to select ions having desired mass and charge from undesired ions. The ion beam is focused in the plane of an aperture 5 as a mass resolving assembly. As known in the art, different ion species in ion beam 2 are deflected through different angles by the mass analyzer 4. A desired ion species passes through the aperture 5 to target 10, while undesired ion species are intercepted by the walls 5' of aperture 5. The ion beam 2 passing through aperture 5 is then accelerated to a desired energy by an accelerator 6, such as a high voltage coil, and is incident on the target 10 located within target chamber 7.

As known, the ion beam 2 can be distributed over the surface of the target 10 by mechanically scanning target 10 with respect to the beam, or vice versa, or a combination of these techniques. For instance, the workpiece target 10 can be moved relative to the ion beam through mechanical or electrostatic means. This ensures that the implant is done uniformly across the workpiece 10, and that the workpiece 10 does not overheat from the high power density being delivered by the beam. The beam 2 typically is directed to a beamstop area (not shown) when the workpieces 10 are not being implanted. The workpiece 10 must be overscanned; i.e., the beam 2 usually goes fully off the workpiece 10 during each scan. In this case, the beam 2 travels beyond the workpiece 10 and strikes a graphite plate, where it is stopped. The target chamber 7 also can include a known system for automatically loading semiconductor wafers into one or more target positions. The entire region between the ion source 1 and the target 10 is maintained at high vacuum during ion implantation.

The ion implanter equipment 100 has inner structural surfaces that are exposed to, and subject to wear, by the high energy ion beams 2. These inner surfaces of the ion implanter are usually made of metallic materials, such as stainless steel or aluminum. Stainless steel, for instance, contains iron, nickel and chromium constituents, which, as with the aluminum, can contaminate the semiconductor devices if these inner surfaces are eroded, and the removed material is transported to the target and implanted into the semiconductor devices. The consequences of this contamination of the wafer are very severe. The resulting semiconductor devices will have degraded performance, reliability, and functionality, such as having high device leakage and defective oxides.

As a conventional approach to dealing with this problem, inner surfaces of the ion implanter apparatus 100 that are known to be subject to ion beam erosion have been covered with graphite, which in small quantities does not seriously affect semiconductor device performance. For instance, the ion beam is rastered across many different parts of the beamline during beam tuning and beam set-up. These parts usually are graphite-coated metal parts, such as graphite-coated stainless steel. The graphite coating has varying thickness, depending on the location in the vacuum processing tool, generally averaging about ¼ inch (about 6.4 mm) in thickness. These graphite-coated metal tool parts are designed to be replaced periodically, viz., before the graphite is worn away and underlying metal is exposed, and becomes eroded or sputtered. However, if this periodic change-out does not occur as scheduled, or a defect is missed during routine maintenance inspections for erosion, or an anomalous wear rate occurs (e.g., due to species mix or liner material variation), or new areas become exposed due to subtle changes in beam column alignment, magnetic fields, new species, or vacuum leaks, then the metal atoms in the metal underyling the graphite coating can become eroded away by the ion beam and become contaminants within the system.

A specific known application of a graphite-coated tool part in the ion implantation system 100 involves the aperture or other apertures used along the beam path, such as aperture 5. The aperture 5 is in the form of a solid plate having an opening Q coincident with the beam line. With reference to FIG. 1B, such an aperture 5 has been made of an aluminum or stainless steel substrate plate 5b covered with graphite 5a to prevent sputtering of the metal 5b by the ion beam 2. Only the part of the beam 2 that is aligned with the aperture opening Q will be passed on down the beamline of the implanter, and the remainder of the beam 2 impacts the graphite plate 5a and is blocked. Again, sputtering of the outer graphite coating 5a in small quantities poses little risk of contamination problems to the semiconductor devices being formed in the wafer. However, as shown in FIG. 1C, over time, the outer graphite covering 5a eventually is worn away by high energy ion beams used for processing within the tool 100 to expose the underlying metal substrate 5b of the aperture 5. Once exposed, the underlying metal 5b is undesirably sputtered and its constituents volatized and implanted into the wafer 10 raising the risk of failures in the chip devices. Also, as seen in FIG. 1C, the size of opening Q in the eroded aperture 5 tends to increase with time as it is eroded by the beam 2. This causes the beam to increase in cross-sectional area 11, which is undesirable.

Figure 2:
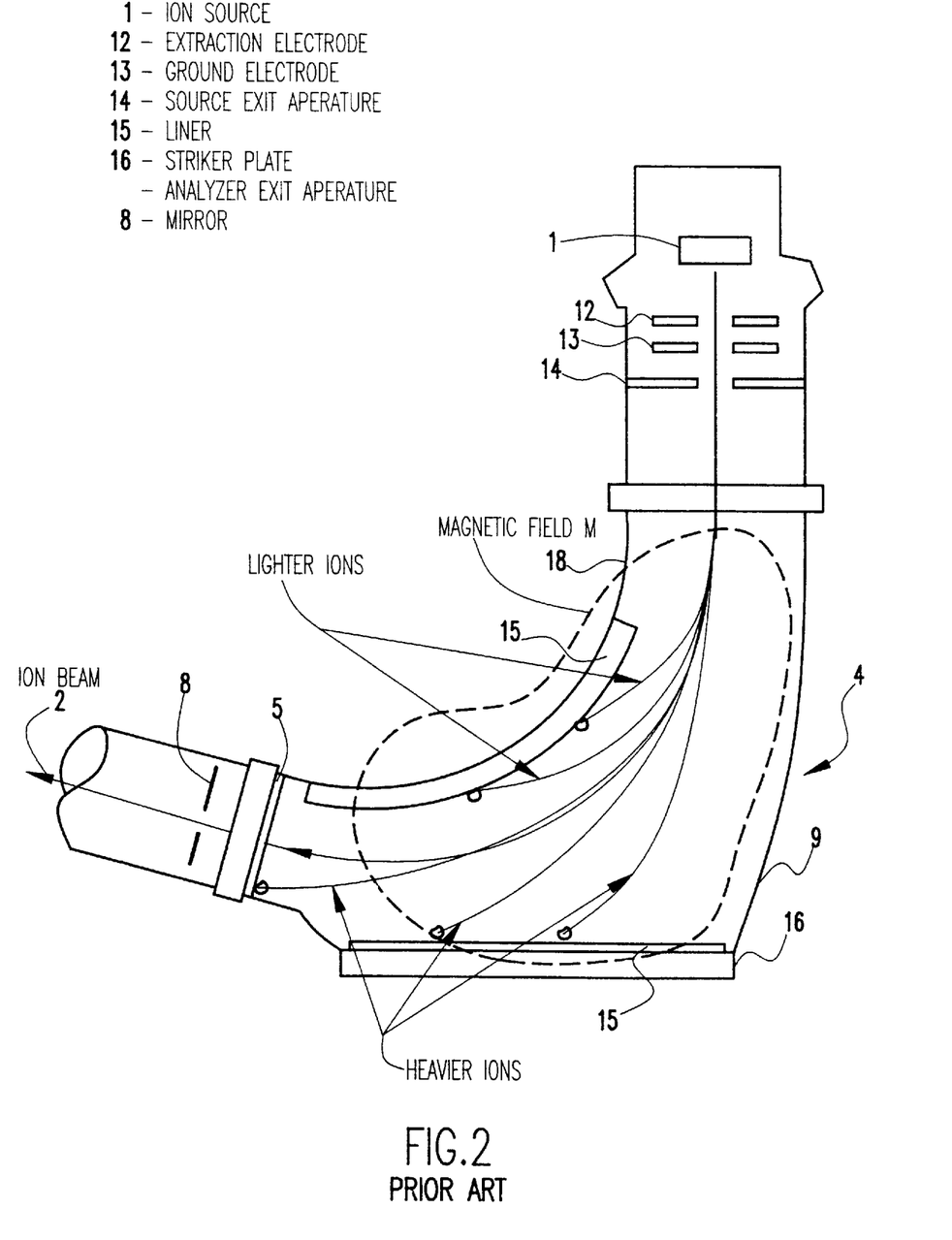
FIG. 2 is an enlarged partial cross sectional side view of the known ion implantation device of FIG. 1A showing details of the mass analyzer component, among other things.

Another specific problem area occurs in the mass analyzer 4. As shown in more detail in FIG. 2, the ion beam 2 enters a region of high magnetic field "M", caused by the analyzer magnet 4. This field region M exerts a force tangential to the direction of travel of a given ion. The ions are displaced from their straight-line path in an amount proportional to their charge, proportional to the magnetic field, and inversely proportional to their molecular weight. The magnetic field strength is adjusted so that the path of the desired species is curved a given amount from the original direction of travel. The inner chamber surface 18 of the mass analyzer 4 has been covered with a thin graphite (or silicon) liner 15 and a striker plate 16 also having a graphite liner 15 has been used on the outer wall 9 of the mass analyzer 4. A conventional arrangement of magnets, not shown, are located with magnetic cores facing the chamber walls 9, 18 of mass analyzer 4. The beam of the desired species is directed through aperture 5, previously discussed in connection with FIG. 1A, which is small enough such that only the desired ionic species is transmitted through it. The desired ion beam is, after passing analyzer exit aperture 5, very pure chemically and has a very tight energy distribution. The direction of the ion beam is fine-tuned through the use of quadruple electrostatic lenses 8 located downstream of accelerator 6. The ion beam 2 then enters the target process chamber 7, as discussed above, where the actual workpiece to be implanted is held. Here again, the graphite liner coatings 15 provided on the inner chamber walls of the mass analyzer 4 can become eroded completely through by action of the ion beam 2 to allow undesired erosion of the underlying steel substrate surfaces.

A residual gas analyzer (RGA) 17, as indicated in FIG. 1A, has been used to detect vacuum system problems or outgassing of particular constituents from a workpiece layer of an implantation (end) chamber of an ion implantation system. A residual gas analyzer is a piece of equipment that withdraws gas from a vessel and ionizes the withdrawn gas sample. The resulting ionized beam is accelerated, and run through a mass analyzer. The mass analyzer involves a region of high magnetic field, the strength of which is adjustable by adjusting the electric current through coils of the magnet. The trajectory of the ion beam being analyzed is curved by the magnetic field, in proportion to the field strength and the charge to mass ratio of the ion. The ion beam is then directed towards an aperture plate, similar to that found in an ion implanter. The portion of the beam curves so that it is aligned with the centerline of the aperture, passes through the aperture, and all other portions of the beam are blocked from traveling further. The intensity of the beam at this given magnetic field setting is measured. A spectrum, or distribution of intensity versus charge to mass ratio, can be obtained by varying the magnetic field strength. The composition of the gas in the vessel can be determined by analyzing this spectrum, and comparing it to the mass/charge ratio of known materials. RGAs are used to detect leaks, and analyze processes. For example, as a known practice, if abnormal amounts of $H_2O$, $O_2$, and $N_2$ are detected, in ratios proportional to those of normal air, then a vacuum leak is suspected. Also, helium has been applied to the exterior of the vacuum processing tool with a suspected leak. If there was a leak, the helium is drawn into the vacuum chamber, and the RGA would then quickly signal the presence of high amounts of helium in the vacuum chamber, signifying that there is a leak in the suspect region of the equipment. An RGA has also been used for troubleshooting vacuum and process problems, by showing the presence of abnormal materials, relative to normal operation, and the type and quantity of these abnormalities. Also, RGA's have been used for end point detection in dry etch tools.

However, there currently is no real-time method for determining if and when the graphite coatings or other protective tool part liners provided on vacuum processing tool parts have become worn through.

Numerous other techniques have been used to analyze constituents of plasmas, and of materials in vapor or gaseous form. These include various forms of spectroscopy, where emitted light (as from plasma) or transmitted light (as through a gas or other fluid) are analyzed and correlated to the absorption or emittance spectra of known materials. The presence of certain wavelengths indicates the presence of a given material, the intensity at that wavelength is related to the concentration of that material, UV, visible light, and IR spectra are commonly used to characterize constituents of plasmas, gases, vapors, and liquids.

SUMMARY OF THE INVENTION

The present invention relates to wear-through detection in multilayered parts. In one particular embodiment, this invention encompasses wear-through detection in semiconductor vacuum processing systems in which a wear indicator that will release a detectable constituent upon exposure to processing conditions is integrated into the vacuum processing tool. This invention permits real time detection of wear during operation of semiconductor vacuum processing equipment.

The invention is generally applicable to semiconductor vacuum processing equipment, including equipment for additive processing such as ion implantation or sputter deposition, as well as equipment for subtractive processing such as dry physical etching (e.g., ion beam etching, sputter etching), reactive ion etching, or dry chemical etching (e.g., plasma removal of photoresist).

As one specific embodiment of this invention, an ion implanter system includes a wear indicating layer in a tool part subject to ion beam attack, in which the wear indicating layer is located between the metal of a tool part and a top protective layer formed thereon exposed to processing species inside the processing tool. A residual gas analyzer or other suitable detection means is used in conjunction with the wear indicator layer to warn that the outer protective coating has been worn through at the detection of the onset of erosion of the underlying indicator layer. This prevents contamination of the implanted layer of the workpiece as the system can be shut down and serviced/repaired before the metal tool part is sputtered.

In a further embodiment, the detection of ion beam wear through the carbon (e.g., graphite) coating is detected by providing an indicator-containing material layer sandwiched between the carbonaceous surface coating and the underlying metal support structure of a tool part. This indicator material is a substance that contains an element, isotope, or molecule that is not otherwise present in the vacuum processing system. The presence or absence of this element in a residual gas analyzer (RGA) spectrum or other suitable detection means informs an operator whether there is any site(s) inside the processing tool where the protective carbon coating on a metal tool part has worn through. If the indicator element is detected by the RGA, then the tool can be shut-down and thoroughly inspected before proceeding with further processing in order to ascertain where the carbon has worn through, and to replace the worn parts.

Care is taken to ensure that the implant source material used in ion implantation of the workpiece does not include the wear indicator element. The indicator material is selected as one which is harmless to the process tool equipment and also the workpiece. It must not adversely affect equipment operation, process results, or workpiece attributes. The indicator material is selected as being one that an RGA can detect at very low levels, or, alternatively, the indicator material can be applied at higher levels without fouling the tool or workpiece.

This invention can also be extended to other semiconductor vacuum processing tools, such as sputtering (deposition) apparatus and plasma etch apparatus. For instance, the invention can also be practiced by locating the indicator layer in the cathode plate member between the backside of a sputtering target and a metal backing (cooling) plate, or, alternatively, the indicator layer can be sandwiched within the thickness of the sputtering target per se at a desired depth. This will prevent the erosion of the target from reaching the metal backing plate, typically stainless steel.

Also, in a reactive ion etch (RIE) tool, the indicator layer of the present invention can be located in-between the metal substrate of the etch chamber wall and an alumina anodization surface layer to prevent operation after the alumina liner has been compromised. A similar utility is similarly applicable to the target chamber of an ion implant tool. The invention is also applicable to indicating the end point of plasma removal of photoresist, such as a plasma ashing process, in which the indicator layer is located in-between the resist layer to be stripped by oxygen plasma and the underlying substrate for which protection from inadvertent plasma etching during resist stripping is desired.

These and other objects and features of the invention will become more fully apparent from the several drawings and description of the preferred embodiments.

BRIEF DESCRIPTION OF THE DRAWINGS

FIG. 6 is a cross sectional view of an otherwise known mass analyzing region of an ion implantation system except that it has been retrofitted according to another embodiment of this invention to include an indicator material placed between a silicon liner and a chamber wall of the mass analyzing region, allowing detection of silicon liner wear-through.

DETAILED DESCRIPTION OF THE PREFERRED EMBODIMENTS OF THE INVENTION

The indicator structures and detection methodology of this invention provide a technique for determining, in real-time, when protective surface layers disposed on multilayered parts have been eroded and thus thinned to an unacceptable extent to threaten exposure of the underlying metal support to an environment which otherwise would erode or corrode the metal, and to signal when replacement of these protective liners is required, or when a process implemented by equipment using such multilayered parts should be halted.

By way of general example, in the context of ion implanter implementations of this invention, the indicator material is disposed beneath at least a portion of the thickness of a protective surface liner used for metal tool parts in semiconductor vacuum processing, such as a carbonaceous material (such as graphite), or silicon. Once the outer protective liner material is eroded sufficiently through its thickness to expose the underlying indicator material, a detectable constituent of the indicator material is liberated (e.g., volatized). These liberated indicator material constituents then become a component of the gases present in the ion implanter system, and it is detected by analytical equipment at the end chamber (i.e., the target chamber) dedicated to monitoring for the presence or absence of the indicator material as at least one of its assigned tasks. A detector, such as a residual gas analyzer (RGA), plasma probe, or an IR, UV or visible light analyzing spectroscope, can be used to detect the presence of these indicator materials and indicate that one of the tool liners has been compromised and that maintenance should be performed to correct the situation before unacceptable impurity levels are reached. The detector equipment and manner of its operation to conduct the qualitative analysis of the semiconductor vacuum processing gas include those of a conventional nature, such that described in U.S. Pat. No. 5,146,098, which teachings are incorporated herein by reference.

The indicator materials used in practicing this invention must meet certain criteria, listed below:

(1) The exposure of the indicator material must be detectable by some means. Some options for meeting this criterion are:

(i) The indicator material or it's components become volatilized and detected as a part of the vapor present in the equipment when the indicator material is exposed to wear.

(ii) The indicator material catalyzes a chemical reaction when exposed, the control system will measure the presence of reaction products or the reduced quantity of reaction precursors and indicate changes in these quantities.

(iii) The indicator material reacts with gas or liquid in the system, the control system measures the presence of reaction products or the reduced quantity of reaction precursors;

(2) The indicator material must not be otherwise present in the system in significant quantities, such that the addition of a quantity of material from erosion, or exposure, of the indicator layer is not detectable due to high background levels of the materials being measured; and (3) The indicator material should be harmless to the process equipment, and workpiece. It must not adversely affect equipment operation (corrosion), process results, or workpiece attributes.

Examples of useful indicator materials are described below.

For gas-phase based indicator systems, materials can be used with volatile components that can be detected with an RGA, plasma probe techniques, or spectrographic methods (IR, UV spectroscopy). Such indicator compounds include polymeric halogenated hydrocarbons; organic sulphur compounds; noble gases (such as helium, argon, neon, xenon, or krypton) encased in rigid, low permeability foam; deuterium-containing compounds; and polymers containing functional groups that will be decomposed into readily identifiable subcomponents that are not otherwise found in the vacuum system, such as alcohols, ammonia, sulphur compounds, $CO_2$, and the like. Examples of appropriate halogenated hydrocarbons include poly-2,4,6-tribromostyrene and poly-2,4,6-triiodostyrene. Especially useful indicator materials for ion implanter implementations include compounds not normally encountered in the implantation system such as deuterium, sulphur, fluorine, chlorine, bromine or iodine, gallium and the like.

One preferred example of the indicator material is poly-2,4,6-tribromostyrene. Polytribromostyrene has three bromine atoms for every eight carbon atoms in the molecule. The molecular weight of poly-2,4,6-tribromostyrene can be high, so that it does not off-gas under normal semiconductor processing conditions, and its softening point is greater than 220° C. so that it is capable of tolerating typical implanter temperatures. For example, poly-2,4,6-tribomostyrene can be obtained with a molecular weight of 22,000. Also, this material is soluble in many hydrocarbon solvents for ease of handling and it can be applied by coating or painting it upon a metal. Thereafter, the indicator coating is overcoated with a carbon coating, such as graphite, to a thickness, which when depleted, will be defined as excessive thinning for the implementation at issue.

Figure 9:
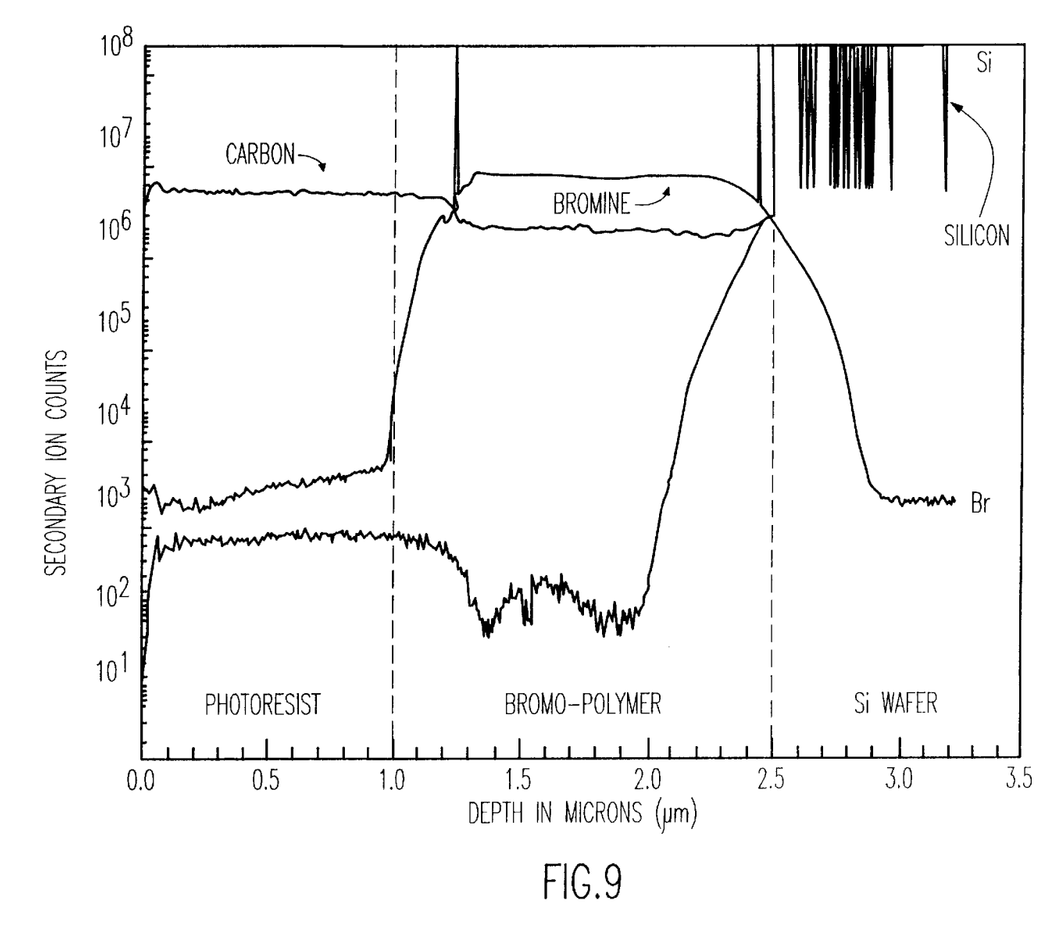
FIG. 9 is a graphical illustration of secondary ion counts made by SIMS for each of carbon, bromine and silicon and plotted as a function of sputter depth into a multilayer laminate formed of a photoresist overcoat, a poly-2,4,6-tribromostyrene indicator layer, and a silicon wafer, in that order.

The utility of poly-2,4,6-tribomostyrene, for example, as an indicator layer material used according to the invention, has been demonstrated by preparation of a laminate film stack of a 1.5 µm thick poly-2,4,6-tribomostyrene layer, on a silicon wafer substrate, using a 1.0 µm thick APEX type photoresist overcoat on the poly-2,4,6-tribromostyrene layer. This arrangement provided a carbon-containing, non-bromofunctionalized overlayer on top of a bromo-containing detection layer, i.e. the poly-2,4,6-tribromostyrene layer. This stack was submitted for SIMS analysis where a sputtering beam hit the film surface and the ejected ions were monitored by secondary-ion mass spectrometry (i.e., SIMS). As illustrated graphically in FIG. 9, secondary ion counts were made by SIMS for each of carbon, bromine and silicon and plotted as a function of the sputter depth into the multilayer laminate including the bromo-containing polymeric detection layer as the middle layer. Vertical hatched lines in FIG. 9 indicate where the layer change-overs occurred relative to the various photoresist, bromo-polymer, and silicon sections, as the sputtering progressed through the thickness of the multilayer laminate. The SIMS results confirmed that the initial photoresist overcoat ejected no bromine ions through its sputtered thickness of 1 µm. However, when the sputtering reached the film interface of the photoresist overcoat layer and the underlying poly-2,4,6-tribomostyrene layer, detection by SIMS of bromine increased sharply to a very high level, which continued to release through sputtering of the poly-2,4,6-tribomostyrene layer, and then bromine detection abruptly stopped when the polymer bromo-containing layer was cleared and the underlying silicon substrate was reached. Carbon traces were also detected through the thickness of the poly-2,4,6-tribomostyrene, as would be expected, in view of the carbon content of the styrene constituent thereof. The results demonstrated the tribromostyrene polymer is stable to vacuum and sputter systems, and that it does not spontaneously decompose until the sputter energy hits the material, at which point high sensitivity detection is possible. Also, the overlying film can be decomposed without affecting the tribomostyrene polymer.

For liquid-phase based indicator systems, materials can be used that contain insoluble components not otherwise present in the system. For example, useful materials as indicators in this respect are those that catalyze liquid tracer decomposition or reaction (i.e., Pt), those indicators that react with liquid tracer materials, and those indicators that change pH of a stored liquid.

More detailed descriptions of implementations of this invention are set forth hereinafter.

Figure 3A:
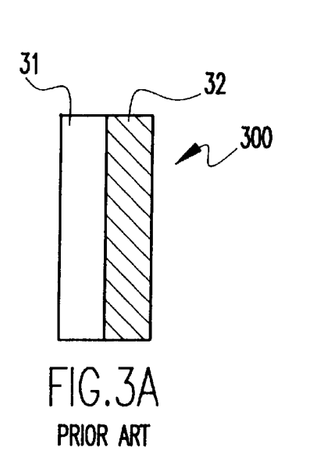
FIG. 3A shows an enlarged cross section of a striker plate (beam stop) lacking an indicator liner according to the present invention.
Figure 3B:
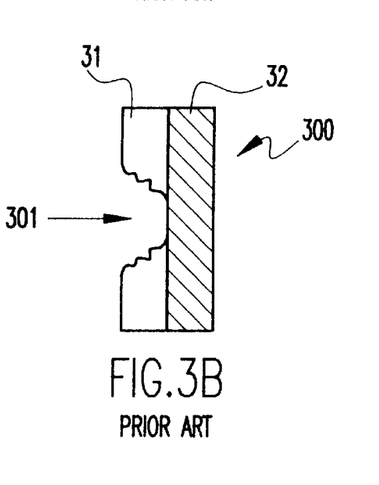
FIG. 3B shows the striker plate worn through to expose underlying metal.

FIG. 3A shows a conventional striker plate (beam stop) 300 having a metal backing plate 32 (e.g., aluminum) and a graphite liner 31. As FIG. 3B shows, the striker plate 300 is worn through graphite layer 31 by ion beam 301 to expose the underlying metal 32 (e.g., aluminum) and expose it to erosion, which leads to contamination of the workpiece.

Figure 3C:
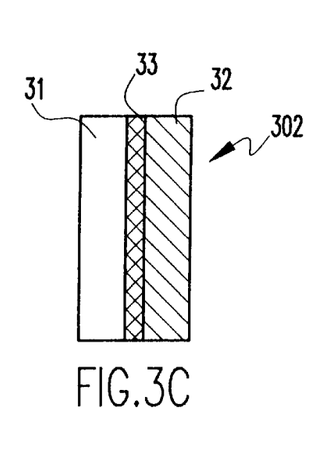
FIG. 3C shows an enlarged cross section of a striker plate (beam stop) having an indicator liner according to the present invention.
Figure 3D:
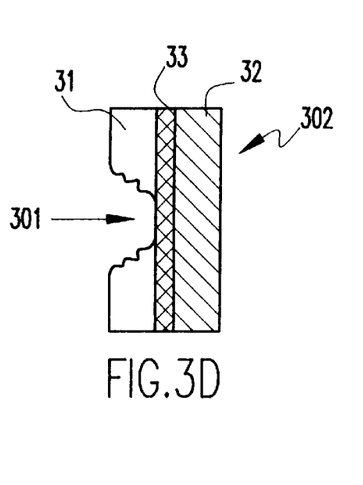
FIG. 3D shows the striker plate worn through to expose the indicator layer, but not the underlying metal.

FIG. 3C shows a striker plate (beam stop) 302 designed according to the present invention with metal backing plate 32 having an indicator layer 33 formed thereon, which in turn, is covered by graphite surface layer 31. The thickness of the indicator layer can vary, e.g., depending on the type of material being used. However, a thickness ranging from about 0.001 to 0.5 inches (0.0254 to 12.7 mm) is generally applicable. FIG. 3D shows the graphite layer 31 of striker plate 302 worn through by ion beam 301 to expose the indicator layer 33, which contains constituents that will be eroded and released upon exposure to the ion beam 301 before metal layer 32 is exposed to ion beam attack. The liberated constituents of indicator layer 33 are detected by a detector, such as a RGA. The RGA analysis is done on residual gas material pumped from the target chamber by a RGA pump into the RGA. For example, FIG. 1A schematically shows a RGA connection to a target chamber that is applicable to the present invention. The RGA performs the analysis of the residual gas material.

Figure 3E:
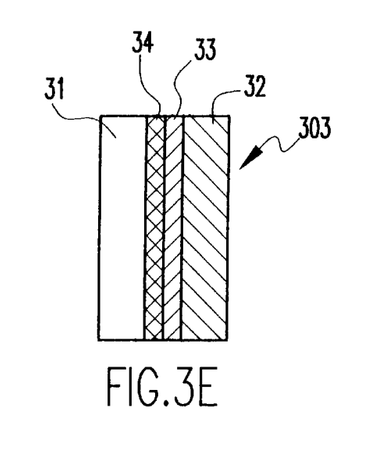
FIG. 3E shows an enlarged cross section of a striker plate (beam stop) having first and second indicator liners according to another embodiment of the present invention.
Figure 3F:
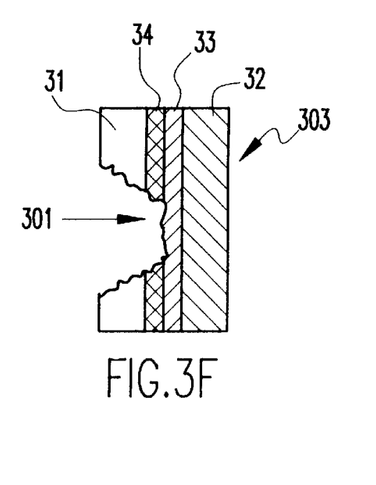
FIG. 3F shows the striker plate worn through the first indicator layer to expose the second indicator layer, but not the underlying metal.

As another embodiment of the invention, FIG. 3E shows a striker plate (beam stop) 303 having first and second indicator liners 33, 34 provided between the metal plate 32 and graphite coating 31, where indicator liners 33 and 34 contain different types of indicator materials from each other. 3F shows the graphite coating 31 and first indicator layer 34 worn through by ion beam 301 to expose the second indicator layer 34 before the metal layer 32 is exposed. The advantage behind using two or more consecutive indicator layers is that the degree of thinning before reaching metal plate 32 can be monitored with greater accuracy.

That is, multiple indicator layer arrangements can be used to show how much wear has occurred in a given area within the ion implanter system. That is, the graphite liner will first wear through, exposing indicator material type #1. This tells the operator that the graphite liner has been compromised, and that maintenance of this area should be performed at the next scheduled time. If maintenance is not performed for some reason, then indicator material type #1 ultimately also will be worn away, exposing underlying indicator material type #2. This should be treated as an urgent signal, and that there is little time left before the underlying critical material is exposed. The user can also use this method to determine the erosion rate of indicator material type #1. The user would determine the first incidence of material type #1 being detected, and the first incidence of material type #2 being detected. The difference in these times is the time required to erode through the layer. The user could also have a sandwich of three or more layers of different respective types of indicators. The user could examine the times that these indicator materials first are detected, and use this to estimate in real-time how quickly the indicator material is eroding.

Figure 4A:
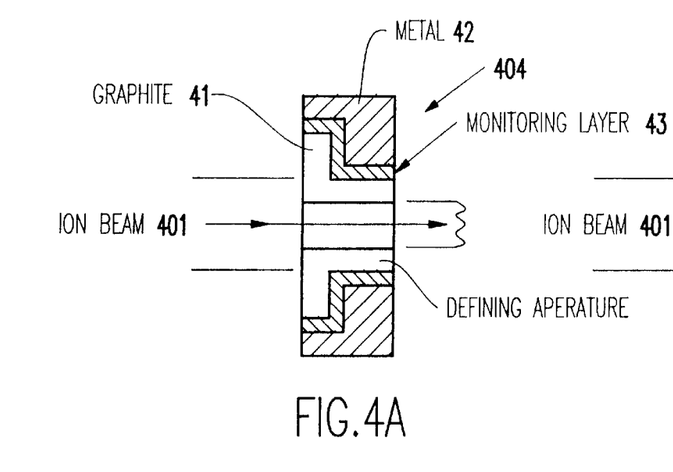
FIG. 4A shows an enlarged cross sectional view of an indicator material layer used in an aperture of an ion implantation device according to an embodiment of the invention.
Figure 4B:
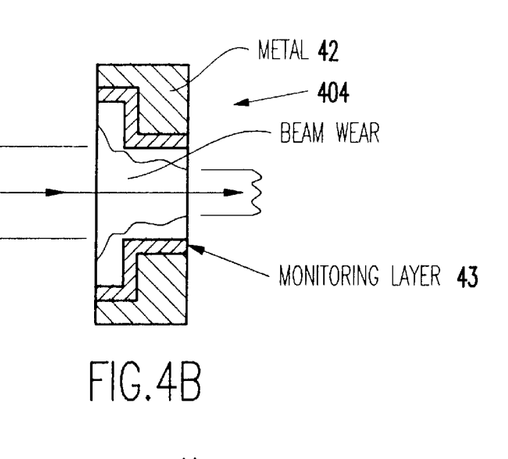
FIG. 4B shows a cross section view after graphite material has been eroded away by the ion beam from the aperture.

In a different implementation of this invention, FIG. 4A shows an aperture 404 having an indicator layer 43 situated between metal substrate plate 42 (such as stainless steel) and the graphite liner 41. The graphite liner typically has a thickness of 0.25 to 0.5 inches (6.4 to 12.7 mm), and the indicator layer 43 used in this implementation generally ranges from about 0.05 to about 0.10 inches (about 1.3 to about 2.5 mm). FIG. 4B shows the erosion of graphite liner 41 caused by ion beam 401 which ultimately exposes portions of the indicator layer 43 to liberate indicator constituents therefrom for detection before the metal plate 42 becomes exposed.

Figure 4C:
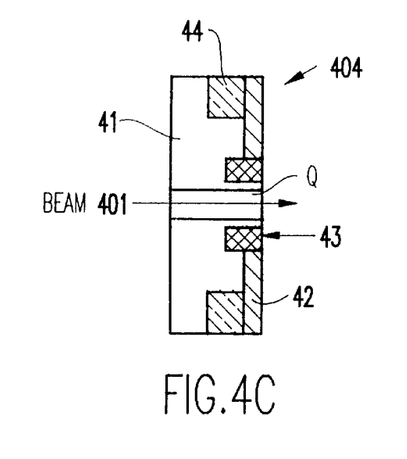
FIG. 4C shows an enlarged cross section of an aperture member having first and second indicator liners according to another embodiment of the present invention.
Figure 4D:
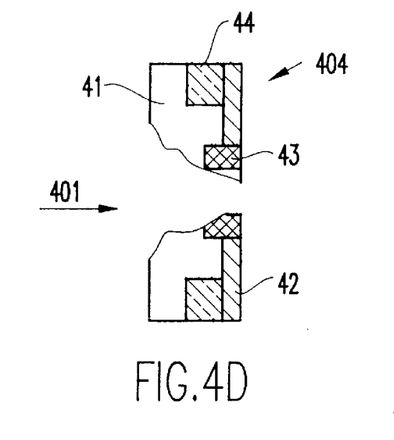
FIG. 4D shows the aperture worn through the first indicator layer to expose the second indicator layer, but not the underlying metal.

FIG. 4C shows another embodiment in which aperture member 404 has first and second indicator layers 43 and 44 containing different types of indicator materials provided at different locations within aperture 404 between the metal back plate 42 and the graphite 41. The first indicator layer 43 is located as an annular structure disposed on metal plate 42 in which the annular indicator layer 44 structure has a larger radius than that of the nominal aperture opening Q such that a portion of graphite 41 fills in the intervening radial space. In service, the opening Q of aperture 404 will be eroded, increasing in radial size until it wears through graphite 41 until it reaches the first indicator material 43. The indicator material 43 is then exposed, eroded by the ion beam, and incorporated into the vacuum ambient. It can then be detected by a RGA, or by other means. When it is detected, it signifies that the opening Q of aperture 404 has eroded to an unacceptable radial diameter, and that the aperture member 404 should be replaced. FIG. 4D shows the aperture 404 worn through the graphite 41 until the first indicator layer 43 is exposed, but not the metal backing plate 42. Also, the metal plate 42 is not required in the embodiment of FIG. 4C as the wear indicators 43 and 44 alternatively can be formed integral with the graphite 41 without the need for a metal support plate 42.

The embodiment shown in FIG. 4A is based on the following concerns. In an ion implanter, the ion beam is not usually a refined gaussian beam, and there are frequently undesired species in large quantities that are close in charge/mass ratio to the desired processing species. In the present invention, two different wear mechanisms are of primary interest. As one, the aperture increasing in size because the spatial distribution of the desired species is wider than desired. In this case, the sides of the aperture opening, and the near edge of the aperture opening are sputtered away by the desired beam. Wear occurring through this mechanism deceases the selectivity/mass resolution of the ion implanter. The operator needs to detect this form of wear before it causes undesired contamination of the ion beam. As the other wear mechanism of interest, the high current non-desired beam, such as encountered when separating boron 10 from a beam of boron 11, that must be separated from the desired beam hits the aperture plate some distance from the aperture itself. This, if it proceeds extensively enough, can cause serious damage to the implant equipment itself. This spurious ion beam can, after it erodes through the aperture plate, erode away the stainless steel chamber wall, introducing metallic contaminates into the implanter vacuum as well causing expensive repairs and equipment down-time.

Another variant of the design of FIG. 4C is to put a layer of indicator material 43 on the downstream side of the aperture plate 404 in lieu of metal plate 42, at a critical distance away from the aperture center.

Also, the invention can be applied to plastic layers used to cover screws used to assemble together the components of the ion implanter or other apparatus in which the wear indicator layer is disposed in-between the plastic covering and a metal screw head.

It is also possible to use different indicator materials at different locations along an ion implant or other system. If multiple wear points exist in the system, and the same indicator material is used, the user will be able to tell if the tool liner is compromised, but will not be able to tell where exactly maintenance is needed. This can be avoided by using different types of indicator materials at different points in the processing tool. For example, an indicator material type #1 could be used in the analyzing magnet region; an indicator material type #2 in the defining aperture, and an indicator material type #3 used in the beamstop region. If the erosion or exposure of one of these materials occurs, then the user can immediately tell which indicator material is exposed/eroded, and which part of the tool is compromised. The user can then target maintenance to the appropriate location within the tool, which will save time and reduce equipment downtime.

Figure 5:
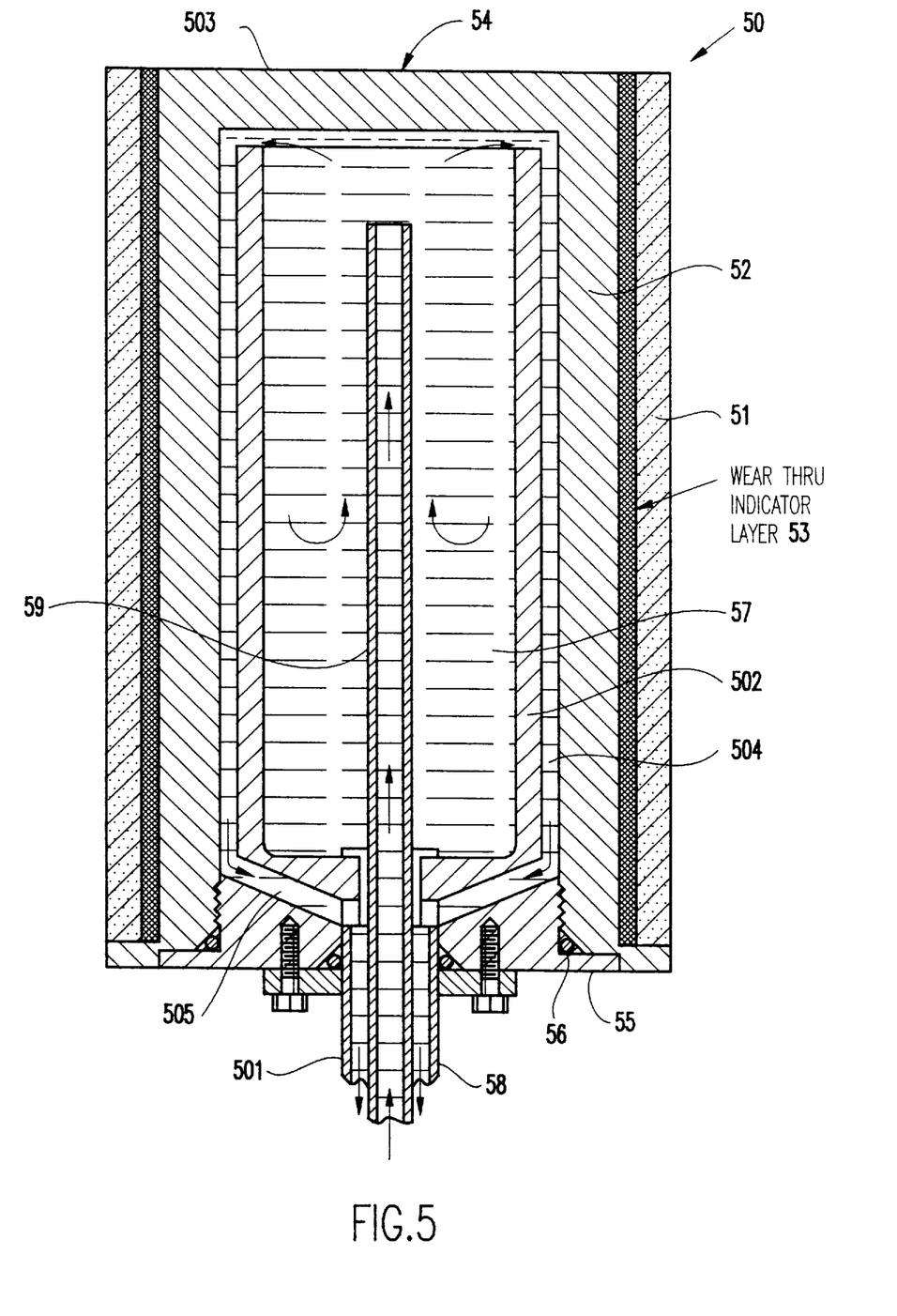
FIG. 5 is an enlarged cross sectional side view of an otherwise known cylindrical mass resolving slit assembly except that it has been retrofitted according to another embodiment of this invention to include an indicator material used to detect wear-through of a graphite layer on the rotating mechanism.

The above exemplifications are by no means exhaustive. The indicator materials and detection means according to the present invention can be readily introduced and retrofitted into many existing ion implanter systems and arrangements to enhance their operation. For example, U.S. Pat. No. 5,629,528 introduces the use of a pair of rotating cylinders to serve as the defining aperture in an ion implant system. These are metal cylinders, cooled internally, that are covered with graphite. The thickness of this graphite is critical, as it's erosion will change the effective aperture size. If the graphite wears through, then the underlying metal will be exposed and eroded by the ion beam. The wear-through of the graphite will expose an indicator material, causing it to be eroded and detected by RGA or other means. As shown in FIG. 5, a mass resolving cylinder 50 of the general type described in U.S. Pat. No. 5,629,528 is redesigned to include an indicator material 53 according to this invention placed between the outer sleeve of graphite 51 and the underlying metal cylindrical sidewall 52 of metal shell 53, e.g., an aluminum shell. Other depicted features of the cylinder 54 are important to its operation, but are not particularly relevant to the above-described inventive re-design of the cylinder. For instance, a cap 55 is threaded into the lower end of metal shell 54 and sealed thereto by elastomer ring 56. The shell 54 defines an interior volume for circulation of cooling fluid. The shaft 58 is attached to cap 55 and has a coaxial construction including an inner tube 59 and an outer coaxial tube 501. The inner tube 59 extends to the upper portion of interior volume 57. The cylinder 54 also includes a cylindrical baffle 502 mounted within interior volume 57, and the baffle 502 is concentric with metal shell sidewall 52 and extends to a point slightly below top wall 503 of shell 54. A cylindrical passage 504 is defined between sidewall 52 and baffle 502, and passage 504 is connected via a passage 505 to outer tube 501 of shaft 58.

Other construction details and manners of operating the cylindrical mass resolving device are described in U.S. Pat. No. 5,629,528, which teachings are incorporated herein by reference.

The use of the indicator layer 53 in this manner improves this alternative rotating cylindrical type of mass resolving system by allowing maintenance only to be done when necessary, and by offering real-time control of liner wear.

Figure 6:
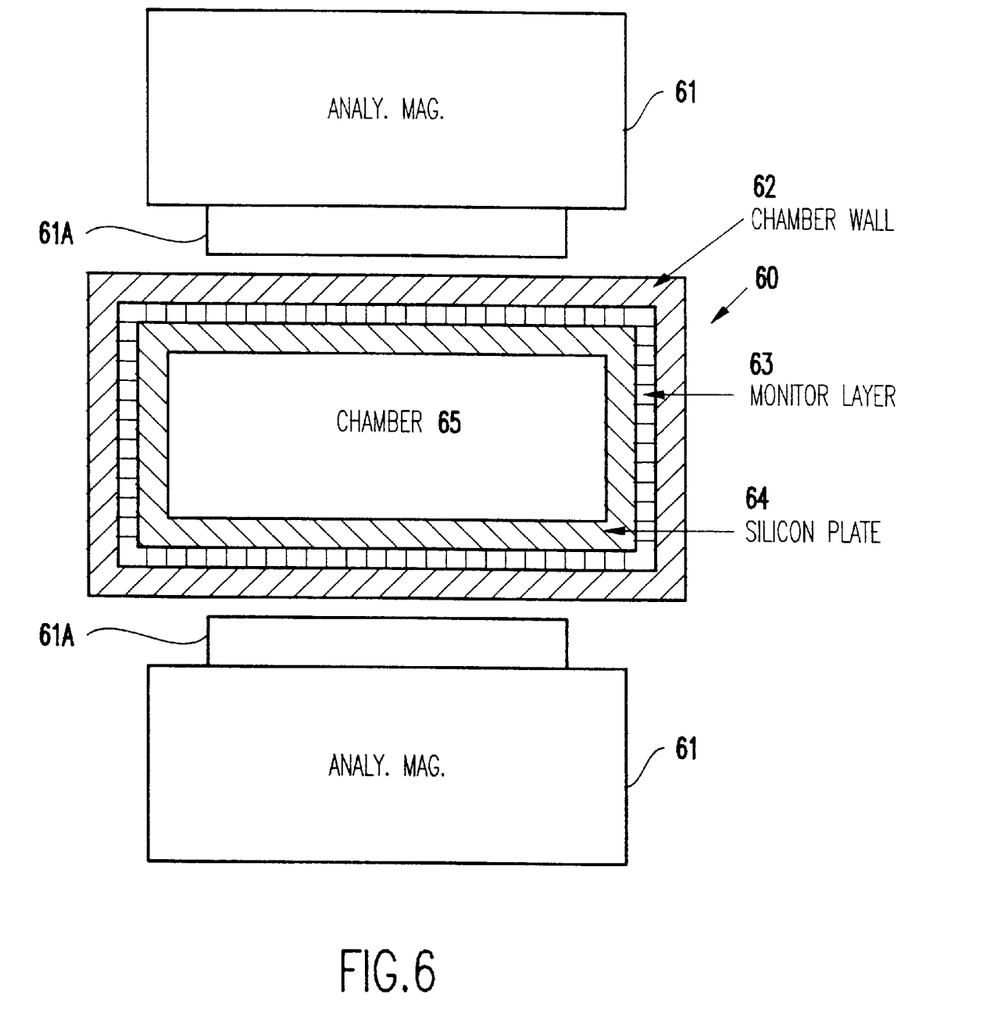

Another implementation of the indicator layer of this invention involves a retrofitting of an ion implanter system such as described in U.S. Pat No. 5,396,076. Namely, as shown in FIG. 6, a mass analyzing region 60 of an ion implant apparatus is shown which selects ions having the predetermined mass. The mass analyzing region 60 has a pair of analyzing magnets 61A located at an upper and lower portion of the mass analyzing region 60, respectively, each having a magnet core on a surface thereof facing a metal chamber wall 62 defining a chamber 65 through which an ion beam travels in the ion implanter system. The inner surfaces of chamber wall 62 are covered with an indicator layer 63, preferably the portions of chamber wall 62 contacting the upper and lower magnets 61. Then, the inner surface of the indicator layer 53 is covered with a thinned silicon plate or lining 64. Placement of the indicator material between the silicon liner 64 and the underlying metal wall 62 provides means to determine when the silicon liner 64 has been compromised. This again offers real-time detection of potential contamination.

The use of indicator material for tool part thinning detection also applies to many other semiconductor vacuum processing toolsets.

Figure 7A:
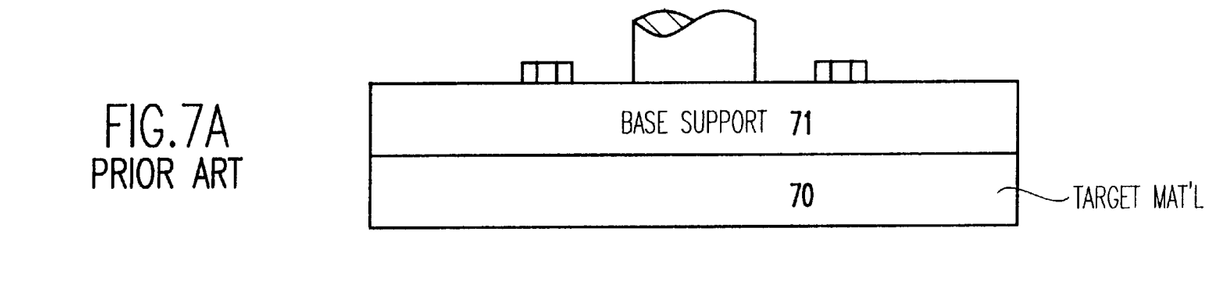
FIG. 7A shows a cross sectional view of a conventional sputtering target lacking an indicator layer according to this invention.

For example, the indicator material can be situated between a sputter target material and target support/cooling plate to indicate when sputter target has been worn through. Sputter tools have a target which contains the material to be deposited. FIG. 7A schematically shows a conventional sputtering target 70 mounted on a metal base support 71, e.g., a stainless steel support. The sputtering target 70 is eroded by the action of the sputtering working ions upon the target. The deposition material atoms then migrate to the workpiece, where they are deposited. There is a finite amount of material present in each target. The target is worn unevenly, due to the differences in magnetic and electrical fields within the process chamber. It is critical that the target be replaced before it is fully worn through in any location. If this is not done, than components of the target backing plate will be deposited on the workpiece, adversely affecting product workpiece functionality. On the other hand, avoidance of premature replacement of targets is desired from cost and down time standpoints.

Figure 7B:
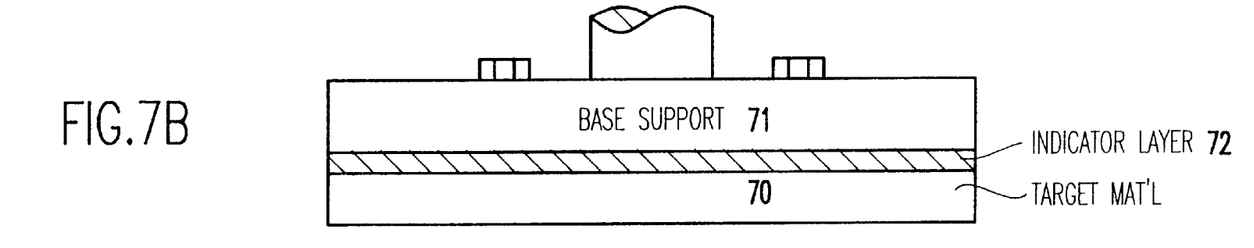
FIG. 7B shows a cross sectional view of a sputtering target having an indicator layer according to this invention.
Figure 7C:
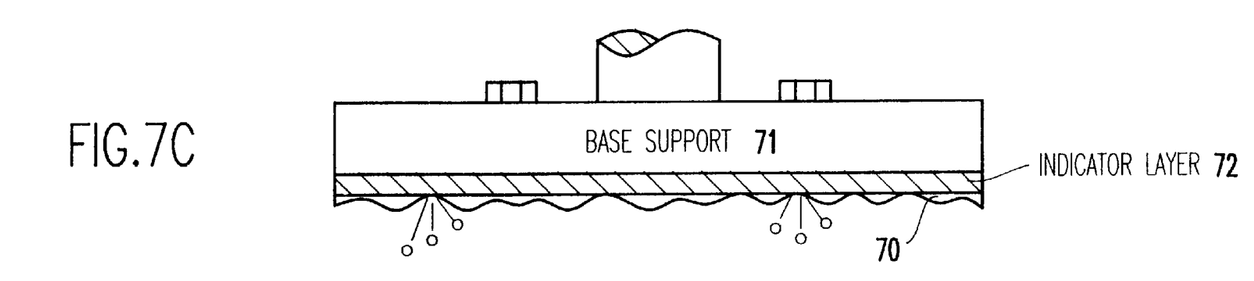
FIG. 7C shows a cross sectional view of a sputtering target having an indicator layer according to this invention after sustaining some target erosion.

The present invention satisfies these concerns by placing an indicator material at some submerged depth within the sputter target per se, or alternatively by placing the indicator material between the sputter target and the backing plate. As shown in FIG. 7B, sputtering target 70 is situated on indicator layer 72, which, in turn, is provided on metal base support 71. FIG. 7C shows exposure of the indicator layer 72 after consumption has occurred through the sputtering target 70. Exposure of the indicator material, and detection of it or it's components in the process chamber, signifies that the target is fully consumed, and needs to be replaced.

Indicator materials useful for the sputtering target implementation can preferably include volatile non-reactive gases (such as the noble series), or similar metals that will not adversely affect product performance if present in small amounts (for example, use Co, Ni, Nb, Pt, Pd, Ir, Rh, Ru, Mo, W, Ta, or Zr). Metal-gas compounds (such as $Al_2O_3$, AlN, TiN, TiO, $TiH_x$, $AlH_x$, $TiD_x$, $AlD_x$) of the nominal target material could also be used. Hydrides and deuterides of these metals are especially useful, as the presence of hydrogen or deuterium ("D") in the final deposited metal is usually harmless. Also, deuterium is not normally present in, and is readily detectable in vacuum, atmospheric, or pressurized systems.

In another implementation involving a different tool set, the indicator layer can be located in-between the metal substrate of the etch chamber wall and an alumina anodization surface layer in reactive ion etching (RIE) tools to prevent operation after the alumina liner has been compromised. A similar utility is similarly applicable to the target chamber of an implant tool.

This invention is also applicable to indicating the end point of processing operations conducted in a semiconductor vacuum processing tool. For example, in removal of the photoresist pattern remaining after completion of a photolithographic patterning operation, the indicator layer can be located in-between the resist layer to be stripped by plasma ashing (viz., using an oxygen plasma) and the underlying substrate for which protection from inadvertent plasma etching during resist stripping is desired.

Figure 8A:
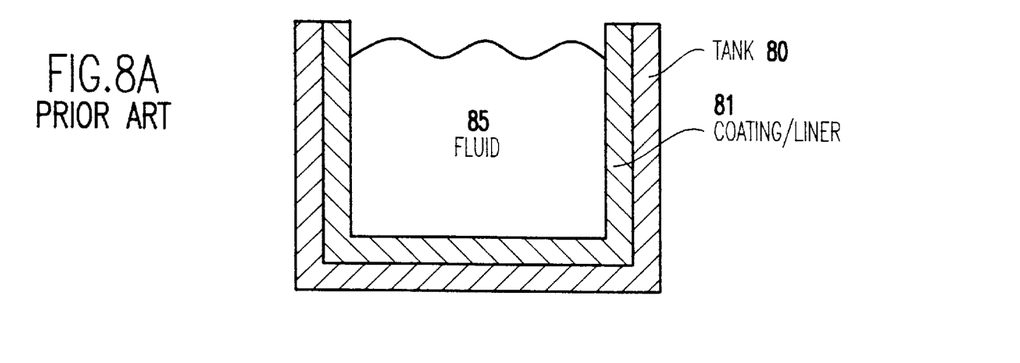
FIG. 8A shows a cross sectional view of a conventional lined holding tank (gas or liquid) lacking an indicator layer according to this invention.
Figure 8B:
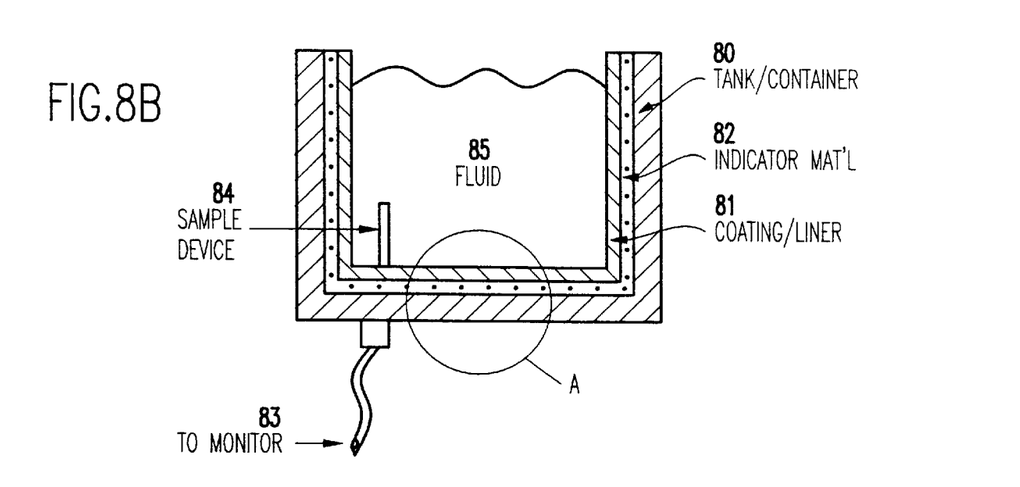
FIG. 8B shows a cross sectional view of a holding tank (gas or liquid) having an indicator layer according to this invention interposed at the interface of the liner and tank wall.
Figure 8C:
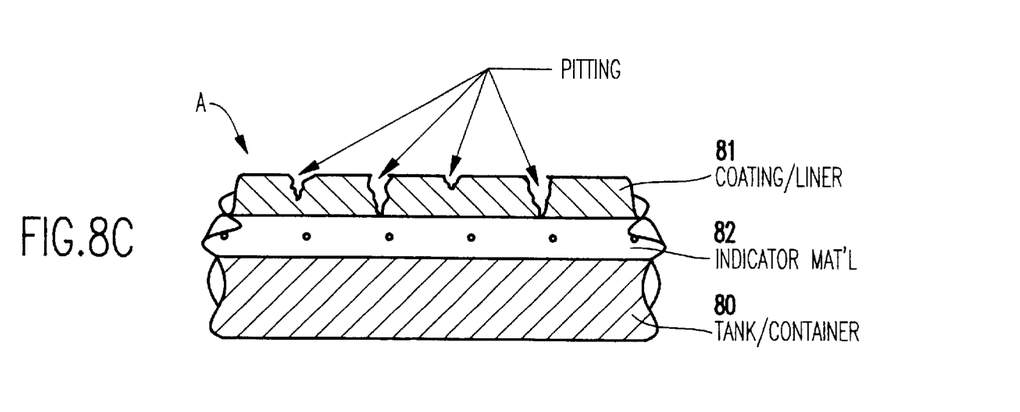
FIG. 8C shows an enlarged view of area A defined in FIG. 8B showing pitting or other corrosion/erosion of the coating/liner/or top layer of the tank material, exposing the indicator material.

As an implementation of this invention, not involving the interior of semiconductor vacuum processing equipment, the indicator material can be located under a storage vessel or tank liner, or at a given depth within the wall of a vessel to indicate when pitting corrosion has occurred. FIG. 8A schematically shows a conventional fluid holding tank (gas or liquid) 80 having a anti-corrosion liner or coating 81. Holding tank 80 can be, for example, a pressurized vessel storing process or reactant fluids 85 to be supplied to a ion implanter, sputtering, or dry etch apparatus. FIG. 8B shows a holding tank 80 having an indicator layer 82 according to this invention interposed either at the interface of the liner 81 and tank wall 80. Alternatively, the indicator layer 82 could be disposed at a set depth within the wall material 80. A sampler device 84 is located within the tank 80 which allows extraction of a small quantity of the stored fluid contents 85 of the tank 80 and feeding the extracted sample via line 83 to an analyzer to monitor for the presence of the indicator material of layer 82. FIG. 8C shows an enlarged view of section A in FIG. 8B showing pitting or other corrosion/erosion of the coating/liner/or top layer 81 of the tank material 80, exposing the indicator material 82.

It is to be understood that this invention is not limited to any particular forms illustrated herein and that it is intended in the appended claims to cover all modifications that do not depart from the spirit and scope of this invention.

What is claimed is:

1. A method of detecting thinning from wear in a multi-layered structure, comprising:

providing an apparatus for processing an electronic workpiece;

providing said apparatus with an indicator layer comprised of a detectable constituent;

exposing said indicator layer to an environment which may erode said indicator layer effective to release said detectable constituent; and wherein if said indicator layer is eroded, said detectable constituent is transported to a detector within said apparatus for processing capable of detecting presence of said constituent and signaling said presence.

2. A method as recited in claim 1, said apparatus further comprising a substrate, said indicator layer being on said substrate.

3. A method as recited in claim 2, further comprising a surface layer, said indicator layer being between said surface layer and said substrate.

4. A method of detecting wear of a structural part of a semiconductor vacuum processing tool apparatus, comprising:

providing a semiconductor vacuum processing apparatus housing at least one structural component comprising, in this sequence, a substrate, a thinning indicator layer located on said substrate where said indicator layer comprises a detectable constituent, and, on said indicator layer, a top layer exposed to contact with processing species within said processing apparatus, said detectable constituent being a compound or heavy isotope;

providing a detector for detecting particles of said detectable constituent;

exposing said structural component to said processing species;

detecting with said detector said constituent when released from said indicator layer by effect of said processing species once said top layer is eroded through exposing said indicator layer; and signaling detection of said indicator layer constituent.

5. The method of claim 4, wherein said top layer comprises a material selected from the group consisting of carbon, silicon, and graphite.

6. The method of claim 4, wherein said detectable constituent is selected from the group consisting of deuterium, sulphur, fluorine, chlorine, bromine, iodine, and gallium.

7. The method of claim 4, wherein said detectable constituent is selected from the group consisting of $CO_2$, $CH_3OH$, $C_2H_5OH$, benzene, phenol, and $NH_3$.

8. The method of claim 4, wherein said detectable constituent, when released from said indicator layer upon exposure to said processing species, is transported to said detector.

9. The method of claim 4, wherein said detector is a selected from the group consisting of a residual gas analyzer and an optical spectrum analyzer.

10. The method of claim 4, wherein said signaling stops further operation of said processing tool apparatus.

11. The method of claim 4, wherein said signaling is used to adjust a process parameter.

12. The method of claim 4, wherein said structural component is an aperture.

13. The method of claim 4, wherein said structural component is a strike plate of a mass analyzer.

14. The method of claim 4, wherein said structural component is a sputtering target.

15. The method of claim 4, wherein said structural component is a chamber wall in a reactive ion etcher.

16. The method of claim 4, wherein said processing species comprise energetic charged ions.

17. The method of claim 4, wherein said processing species comprises an ion beam.

18. The method of claim 4, wherein said processing species comprises a plasma for etching or deposition.

* * * * *